United States Patent
Meade et al.

(10) Patent No.: US 6,780,856 B2
(45) Date of Patent: Aug. 24, 2004

(54) TOWARDS INCREASED SHELF LIFE FOR COBALT(III) SCHIFF BASE COMPLEXES

(75) Inventors: Thomas J. Meade, Altadena, CA (US); Ofer Blum, Ann Arbor, MI (US); Harry B. Gray, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 422 days.

(21) Appl. No.: 09/828,499

(22) Filed: Apr. 6, 2001

(65) Prior Publication Data

US 2002/0013470 A1 Jan. 31, 2002

Related U.S. Application Data

(60) Provisional application No. 60/195,397, filed on Apr. 7, 2000.

(51) Int. Cl.[7] .................. A61K 31/33; A61K 31/295; C07D 265/04; C07D 233/00
(52) U.S. Cl. ............... 514/183; 514/185; 514/501; 544/88; 548/300.1
(58) Field of Search ................... 514/183, 185, 514/501; 544/88; 548/300.1

(56) References Cited

U.S. PATENT DOCUMENTS

| | | | |
|---|---|---|---|
| 5,049,557 A | * | 9/1991 | Dori et al. .......... 514/185 |
| 5,753,698 A | * | 5/1998 | Gershon et al. ........ 514/501 |
| 5,886,032 A | | 3/1999 | Gershon et al. |
| 6,008,190 A | | 12/1999 | Meade et al. |

FOREIGN PATENT DOCUMENTS

| | | | |
|---|---|---|---|
| WO | 9006119 | * | 4/1990 |
| WO | 9006119 | * | 6/1990 |

OTHER PUBLICATIONS

Blum, et al., "Isolation of a myoglobin molten globule by selective cobalt(III)–induced unfolding" *Proc. Natl. Acad. Sci. USA* 95:6659–6662 (1998).

Böttcher, et al., Spectroscopy and Electrochemistry of Cobalt(III) Schiff Base Complexes, *Inorg. Chem.* 36:2498–2504 (1997).

Góral and Nakamoto, "Synthesis and Spectra of Co(Salen) Derivatives Containing Pendant Groups and their Dioxygen Adducts. Pendant Chain Length and Coordinating Ability," *Inorganica Chimica Acta*, 146:193–198 (1988).

Louie and Meade, "A cobalt complex that selectively disrupts the structure and function of zinc fingers," *Proc. Natl. Acad. Sci USA* 95:6663–6668 (1998).

Takeuchi, et al., "Selective Inhibition of Human α–Thrombin by Cobalt(111) Schiff Base Complexes," *J. Am. Chem. Soc.* 120:8555–8556 (1998).

* cited by examiner

*Primary Examiner*—Mukund J. Shah
*Assistant Examiner*—Sidhaker B. Patel
(74) *Attorney, Agent, or Firm*—Gray Cary Ware & Freidenrich, LLP

(57) ABSTRACT

The invention relates to methods of stabilizing in an aqueous medium cobalt (III) Schiff base complexes and stabilized cobalt (III) Schiff base compounds therefrom.

16 Claims, No Drawings

TOWARDS INCREASED SHELF LIFE FOR COBALT(III) SCHIFF BASE COMPLEXES

RELATED APPLICATIONS

The present application claims the benefit of priority to Provisional U.S. Application No. 60/195,397, filed Apr. 7, 2000, herein incorporated by reference in its entirety.

FIELD OF THE INVENTION

The invention relates to methods of stabilizing in an aqueous medium cobalt (III) Schiff base complexes and stabilized cobalt (III) Schiff base compounds therefrom.

BACKGROUND OF THE INVENTION

Certain Schiff base cobalt complexes that exhibit antiviral, antitumor, and antimicrobial activities, as well as showing use in the treatment of inflammation and burns activity are stable for prolonged periods in solid form, but lose activity in aqueous solutions. The loss of activity in aqueous solutions results in loss of efficacy and a shorted shelf life.

A change in composition is responsible for the loss in compound efficacy and activity. When the complexes are in aqueous solutions without additives with good coordinating abilities, complexes such as $[Co(acacen)L_2]^+$, where acacen is 1,2-bis-acetylacetonate-ethylenediimine, L is $NH_3$ or 2-methylimidazole, show axial ligand exchange on the cobalt.

Accordingly, there is a need for methods of stabilizing Schiff base cobalt complexes in aqueous solutions. The stabilized compounds produced by invention methods are useful antiviral, antitumor, antinflammatory and antimicrobial agents.

SUMMARY OF THE INVENTION

In accordance with these objects, compositions are provided comprising water soluble tetradentate Schiff base complexes of Co(III).

DETAILED DESCRIPTION OF THE INVENTION

The present invention is directed to methods of stabilizing Cobalt(III) Schiff base complexes in aqueous media. Invention methods include obtaining Schiff base complexes and adding to the complex a linker or a chelator that binds to at least one axial ligand position of the complex.

As used herein, "Schiff base" refers to a substituted imine. Substituent groups are described herein. Schiff bases are generally the condensation products of amines and aliphatic aldehydes forming azomethines substituted on the nitrogen atom. The cobalt compounds of the invention utilize Co(III) (also depicted herein as Co+3). Co(III) compounds have up to six coordination atoms of which two are defined herein as axial ligand positions (L).

As used herein, "axial ligand position" refers to a ligand position (L) located at the fifth and sixth coordination sites, generally depicted in Structure A below.

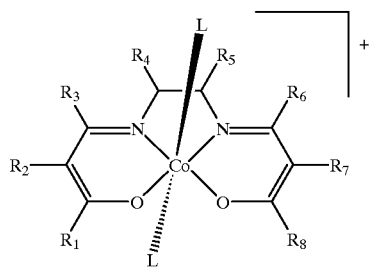

Structure A

Cobalt compounds of the invention derive their biological activity by the substitution or addition of ligands in the axial positions. Preferred ligands in the axial ligand position are nitrogen containing compounds including primary, secondary amines. Exemplary amines include $NH_3$ and heterocyclic nitrogen containing compounds such as substituted and unsubstituted imidazole.

Co(III) Schiff base complexes are stabilized by adding a linker that connects an axial ligand to an atom in the frame of the Schiff base complex. Linker atoms in the frame include atoms at $R_1$, $R_2$, $R_3$, $R_4$, $R_5$, $R_6$, $R_7$ and $R_8$. Especially preferred linker atom sites are at R4 and $R_5$, and preferred sites are at $R_2$ and $R_3$. The resulting pentadentate cobalt compound has five axial ligand positions for binding. The complex thus formed remains monomeric, i.e., there is little or no intramolecule binding. This method makes it possible to increase the concentration of dissociated ligand around mono-aqua complexes.

As used herein, a "linker" refers to a molecule having that binds to more than one site on a complex wherein one site is an axial ligand position. When the linker is bound, a tether is formed that stabilizes the complex.

A linker of the present invention has the formula $-(CH_2)_n-NR"R'"$. Variable "n" can be 1, 2, 3, 4, 5, 6, 7 or 8, resulting in linker moieties of variable length. The length of the linker affects characteristics of the stabilized compound. The linker is able to disassociate at the axial ligand position. A shorter linker, for example when n is 1, 2, or 3, permits the tether to reassociate at the axial ligand position following disassociation more rapidly than when the tether is longer, for example, when n is 4 or 5. Disassociation and reassociation of the linker at the axial ligand position may permit or increase binding of the complex to its target (and thus have an affect on biological activity of the complex) if both axial ligand positions are binding sites that are essential for biological action. Disassociation and reassociation are also affected by the identity of R and R'.

In the linker, R" and R'" are independently selected from hydrogen and substituted or unsubstituted alkyl, substituted or unsubstituted alkenyl, substituted or unsubstituted alkynyl, substituted or unsubstituted cycloalkyl, ester, alkoxy, ether, or R and R' can cooperate to form a substituted or unsubstituted heterocycle optionally having one or more double bonds. In preferred embodiments of the invention, R and R' are both hydrogen. This embodiment is preferred because the bond at the axial ligand position is labile, allowing disassociation and reassociation of the linker. Synthesis of this linker can be readily accomplished by those of skill in the art. In another preferred embodiment, n is 2 and R and R' cooperate to form an imidazole. In yet another preferred embodiment, n is 2 and R and R' cooperate to form 2-methylimidazole.

By the term "tetradentate" herein is meant that the Schiff base complex, which is a ligand for Co(III), has four coordinating atoms. In a preferred embodiment, there are two nitrogen atoms and two oxygen atoms, which serve as coordinating atoms.

By the term "cobalt compound" herein is meant a tetradentate Schiff base complex with a bound cobalt atom. The Schiff base may be substituted or unsubstituted, and the cobalt is Cobalt (III) (Co(III)).

Also provided is a method of increasing the stability in aqueous media of a cobalt(III) Schiff base complex by obtaining a cobalt(III) Schiff base complex and contacting the complex with a chelator that connects first and second axial positions. The chelator can bind covalently to a Co(III) Schiff base complex.

As used herein, "chelator" refers to a compound having the structure:

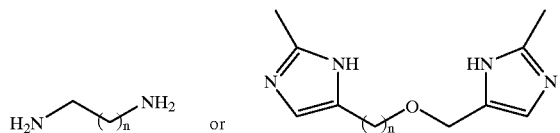

wherein n is 2, 3, 4, 5, 6, 7, or 8. In especially preferred embodiments, n is 2, 3 or 4 and in preferred embodiments, n is 2, 3, 4 or 5.

In one embodiment of the invention, the first axial position and the second axial position are contained in the same Schiff base complex molecule resulting in intramolecular bonds. In another embodiment of the invention, the firs axial position is in a first Schiff base complex molecule and the second axial position is in a second Schiff base complex molecule resulting in intermolecular bonds. When there are intermolecular bonds, two or more molecules are connected by the chelator, resulting in dimers, i.e., two molecules connected by a linker, or resulting in oligomers, i.e., three or more moleucles connected by linkers. Dimers and oligomers can be connected by linkers that are bound at the same axial positions on each Schiff base complex, or that are bound at different axial positions on each Schiff base complex.

For most cobalt complexes, ligand exchange is a slow process because there is a large loss of ligand field stabilization energy when a ligand is removed from an octahedral $d^6$ complex (see Huheey et al., Inorganic Chemistry: Principles of Structure and Reactivity, 4th Ed. Harper Collins, N.Y., chapter 13). Generally, the exchange is slow; for example, [Co(III)(acacen)(NH$_3$)$_2$]Cl in water with excess imidazole exchanges ammonia for imidazole with a half-life under an hour at 25° C., with the rate of exchange increasing with temperature.

As used herein, "hydrocarbyl" refers to straight chain, branched chain and cyclic (i.e., ring-containing) monovalent and bivalent radicals derived from saturated or unsaturated moieties containing only carbon and hydrogen atoms. Straight and branched chain radicals have in the range of about 1 up to 12 carbon atoms and cyclic hydrocarbyl radicals have in the range of about 3 up to about 20 carbon atoms. The term "substituted hydrocarbyl" refers to hydrocarbyl moieties further bearing substituents as set forth below.

As used herein, "alkyl" refers to straight or branched chain alkyl radicals having in the range of about 1 up to 20 carbon atoms; "substituted alkyl" refers to alkyl radicals further bearing one or more substituents such as cycloalkyl, cycloalkenyl, aryl, heterocycle optionally having one or more double bonds, halogen, alkoxy, amino, amide, hydroxyl, carboxyl, ether, ester, sulfonyl, sulfonadmide, and the like. If branched, it may be branched at one or more positions, and unless specified, at any position. In some cases, two alkyl groups may be part of a ring structure; that is, they may be linked to form a cyclic structure.

As used herein, "alkenyl" refers to straight or branched chain hydrocarbyl radicals having at least one carbon-carbon double bond, and having in the range of about 2 up to 12 carbon atoms, and "substituted alkenyl" refers to alkenyl radicals further bearing one or more substituents as set forth above.

As used herein, "alkynyl" refers to straight or branched chain hydrocarbyl radicals having at least one carbon-carbon triple bond, and having in the range of about 2 up to 12 carbon atoms, and "substituted alkynyl" refers to alkynyl radicals further bearing one or more substituents as set forth above.

As used herein, "cycloalkyl" refers to ring-containing radicals containing in the range of about 3 up to 20 carbon atoms, and "substituted cycloalkyl" refers to cycloalkyl radicals further bearing one or more substituents as set forth above.

As used herein, "aryl" refers to mononuclear aromatic rings having 6 carbon atoms and fused ring aromatic radicals having up to about 14 carbon atoms, i.e., polynuclear aromatic radicals; and "substituted aryl" refers to aryl radicals further bearing one or more substituents as set forth above. Aryl moieties include phenyl, benzyl, and naphthyl.

As used herein, "heterocycle" refers to ring-containing monovalent and bivalent radicals having one or more heteroatoms (e.g., N, O, S) as part of the ring structure, and having in the range of 3 up to 20 atoms in the ring. As used herein "substituted heterocycle" refers to heterocycles further bearing one or more substituents as set forth above. Heterocyclic moieties may be saturated or unsaturated containing one or more double bonds, and may contain more than one ring. Heterocyclic moieties include monocyclic moieties such as imidzolyl, pyridine, pyrrole, indole, pyridazine, pyrimidine, pyrazine, piperazine, triazine, thiophene, thiazole, triazole, and the like.

As used herein, "halogen" refers to chloride, bromide, iodide and fluoride radicals.

As used herein, "ether" refers to radicals of the general formula —R'—O—R", where R and R" are independently substituted or unsubsituted hydrocarbyl, or substituted or unsubstituted heteroxycle optionally having one or more double bonds.

As used herein, "ester" refers to radicals of the general formula —C(O))—R and —O—C(O)R, where R is substituted or unsubstituted hydrocarbyl, substituted or unsubstituted heterocycle optionally having one or more double bonds; it is understood that the carbon atom of the ester group may be linked directly to the moiety of which ester is a substituent, or may be linked via a linker, such as substituted or unsubstituted alkylene, alkenylene, arylene, and the like.

As used herein, "hydrophilic organic acid" refers to an alkyl group containing one or more carboxyl groups, —COOH, i.e. a carboxyl acid. As defined above, the alkyl group may be substituted or unsubstituted. Alkyl groups containing from one up to 20 carbon atoms may be used with at least one carboxyl group attached to any one of the alkyl carbons, with alkyl groups having from one to five being preferred. In a preferred embodiment, the carboxyl group is attached to the terminal carbon of the alkyl group. Other preferred hydrophilic organic acids include phosphonates and sulfonates. A preferred hydrophilic organic acid is propionic acid. In a preferred embodiment, only one of the R groups is a hydrophilic organic acid, in a Co(III) complex, this may result in a compound that is neutrally charged, and thus may cross the blood-brain barrier.

As used herein, the term "amine" refers to radicals of the general formula —NRR'. In the present invention, R and R' are independently selected from hydrogen, alkyl or aryl. It is understood that R and R' may cooperate to form a cyclic moiety having a nitrogen atom as a member of the ring; and that the nitrogen atom of the amine group may be linked directly to the moiety of which the amine is a ligand. Preferred amines include those where R and R' are both hydrogen, and where R is hydrogen and R' is alkyl.

As used herein, the term "alkyl amine group" refers to an alkyl with a —NRR' group. As defined above, the alkyl group may be substituted or unsubstituted. Preferred alkyl amine groups are n-propylamine and n-butylamine.

As used herein, the term "alkyl alcohol" refers to an alkyl group with an —OH group. As defined above, the alkyl group may be substituted or unsubstituted. The alkyl alcohol may be primary, secondary or tertiary, depending on the alkyl group. In a preferred embodiment, the alkyl alcohol is a straight chain primary alkyl alcohol, generally containing at least 3 carbon atoms. Preferred alkyl alcohols include, but are not limited to, n-propyl alcohol, n-butyl alcohol, n-pentyl alcohol, n-heptyl alcohol, or n-octyl alcohol.

In addition the length of the alkyl group may be altered either to encourage or prevent the carboxylic acid from "swinging around" to become an axial ligand.

In certain embodiments of the invention, one of $R_1$–$R_8$ is either a polypeptide or a nucleic acid. When one of the R groups is a polypeptide or nucleic acid, it is preferred that only one of the R groups is a polypeptide or nucleic acid. That is, a single R group of the cobalt compound is either a polypeptide or a nucleic acid. In an alternative embodiment, more than one of the R groups may be a polypeptide or a nucleic acid. At least one of $R_1$ to $R_8$ is either a polypeptide or a nucleic acid.

As used herein, the term "polypeptide" refers to a compound ranging from about 2 to about 15 amino acid residues covalently linked by peptide bonds. Preferred embodiments utilize polypeptides from about 2 to about 8 amino acids, with about 4 to about 6 being the most preferred. Preferably, the amino acids are naturally occurring amino acids in the L-configuration, although amino acid analogs are also useful, as outlined below. Under certain circumstances, the polypeptide may be only a single amino acid residue. Additionally, in some embodiments, the polypeptide may be larger, and may even be a protein.

Also included within the definition of polypeptide are peptidomimetic structures or amino acid analogs. Thus for example, non-naturally occurring side chains or linkages may be used, for example to prevent or retard in vivo degradations. Alternatively, the amino acid side chains may be in the (R) or D-configuration. Additionally, the amino acids, normally linked via a peptide bond or linkage, i.e. a peptidic carbamoyl group, i.e. —CONH—, may be linked via peptidomimetic bonds. These peptidomimetic bonds include $CH_2$—NH—, CO—$CH_2$, azapeptide and retroinversion bonds.

As used herein, "nucleic acid" refers to either DNA or RNA, or molecules which contain both deoxy- and ribo-nucleotides. Generally, the nucleic acid is an oligonucleotide, ranging from about 3 nucleotides to about 50 nucleotides, with from about 12 to about 36 being particularly preferred, and at least 21 nucleotides being especially preferred. When the nucleic acid is used solely to confer solubility, the nucleic acid may be smaller, and in some embodiments may be a single nucleotide. The nucleotides may be naturally occurring nucleotides, or synthetic nucleotides, and may be any combination of natural and synthetic nucleotides, although uracil, adenine, thymine, cytosine, guanine, and inosine are preferred. The nucleic acids include genomic DNA, CDNA and oligonucleotides including sense and anti-sense nucleic acids. The nucleic acid may be double stranded, single stranded, or contain portions of both double stranded or single stranded sequence.

A nucleic acid will generally contain phosphodiester bonds, although in some cases, as outlined below, a nucleic acid may have an analogous backbone, comprising, for example, phosphoramide (Beaucage et al., Tetrahedron 49(10):1925 (1993) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawai et al, Chem. Lett. 805 (1984), Letsinger et al., J. Am. Chem. Soc. 110:4470 (1988); and Pauwels et al., Chemica Scripta 96:141 91986)), phosphorothionate, phosphorodithioate, O-methylphosphoroamidite linkages (see Eckstein, Oligonucleotides and Analogues: A Practical Approach, Oxford University Press), or peptide nucleic acid linkages (see Egholm, J. Am. Chem. Soc. 114:1895 (1992); Meier et al., Chem. Int. Ed. Engl. 31:1008 (1992); Nielsen, Nature, 365:566 (1993)). These modifications of the ribose phosphate backbone may be done to facilitate the addition of cobalt compounds, as outlined below, or to increase the stability and half-life of such molecules in physiological environments.

In one embodiment, the polypeptide or nucleic acid is chosen just to confer solubility on the cobalt compound, and thus the actual sequence of amino acid residues or nucleotides is not critical. Alternatively, as outlined below, the amino acid residues or nucleotides can be chosen to target a particular protein or enzyme.

In one embodiment, one of $R_1$–$R_4$ is either a polypeptide or a nucleic acid that is used to target the cobalt compound to a particular target protein. That is, the cobalt compound is covalently linked to a polypeptide or nucleic acid that will specifically bind or associate with a target protein. In one embodiment, the cobalt compound containing a polypeptide as one of the R groups inhibits a protein, which may or may not be an enzyme. By "inhibition of a protein" herein is meant that a biological activity of the protein is decreased or eliminated upon binding of the inhibitor. In the case of enzymes, inhibition results in a decrease or loss of enzymatic activity. For example, polypeptides comprising protease substrates or inhibitors are used as an R group on the cobalt compounds, to form cobalt compounds that will selectively inhibit the protease. Similarly, a cobalt compound containing an R group comprising a nucleic acid that specifically binds to a particular transcription factor is used to selectively inhibit the transcription factor. These targeted cobalt compounds preferentially bind to the target site on the protein, favoring that site over non-specific binding to other sites or other proteins. This makes the resulting compound more effective at lower concentrations since fewer molecules are wasted at other sites and minimizes the side effects due to inhibition of other proteins. Secondary interactions also increase the time spent at the target, giving more opportunity for ligand exchange.

In designing a cobalt compound for a particular protein, it is to be understood that the high affinity of the cobalt compound for an imidazole moiety, or the other possible reactive axial ligand moieties, is such that the cobalt compound need not be a perfect fit in the active site. Rather, what is important is that the cobalt compound be able to approach the target axial ligand moiety. For targeting active site residues of enzymes, for example, the cobalt compounds should generally not be larger than typical enzyme substrates or inhibitors. The gross structure and surface properties of the cobalt compound reagent will determine its outer sphere interaction with the desired biological active site. Specificity in outer sphere interactions is optimized by variations in size, charge flexibility, stereochemistry, and surface properties of the cobalt compound reagent. Thus, in designing an appropriate inhibitor, the characteristics of the protein or enzyme target are exploited. In addition, increasing the local concentration of the cobalt compound at or near the active site of the protein is sufficient to increase the binding of the cobalt compound and thus the inhibition of the biological activity of the protein, effectively decreasing the $K_m$ or $K_i$ values, in the case of enzymatic inhibition.

In one embodiment, at least one of $R_1$–$R_8$ of Formula 1 is a polypeptide. In this embodiment, the polypeptide is chosen on the basis of the target protein or enzyme to be inhibited. For example, when the target enzyme is a protease, the polypeptide will mimic or comprise an enzyme substrate or the reactive site of an inhibitor. When the polypeptide comprises an inhibitor, the inhibitor may be either a reversible or irreversible inhibitor. The sequence of the polypeptide is chosen to allow the binding of the polypeptide to the active site of the protease.

The polypeptide and the site of attachment of the polypeptide to the cobalt compound will be chosen to maximize the interaction of the cobalt with the active site histidine. That is, the polypeptide may be attached to the cobalt compound at the N-terminal end, the C-terminal end, or internally, via one or more amino acid side chains.

As is well known in the art, the active site histidine of many enzymes is close to the S1–S1' position of the enzyme's substrate (or inhibitor) binding site. Examples include the serine and cysteine proteases. Thus, in a preferred embodiment, the polypeptide is chosen to allow optimum interaction of the cobalt compound with the active site histidine. For example, the polypeptide may comprise roughly the P4 through P1 residues of a substrate or inhibitor (which occupy the S4 to S1 positions of the enzyme's binding site), and be attached at the C-terminal end (P1) to the cobalt compound, to maximize the steric interaction of the cobalt compound with the active site of the enzyme, and particularly the active site histidine. Alternatively, the polypeptide may comprise the P1' through P4' residues (corresponding to the S1' to S4' positions). with attachment at the N-terminus (P1'). In a further embodiment, the polypeptide spans the P1–P1' site, but has an internal attachment at or near the P1 or P1' residues, to similarly maximize the interaction of the cobalt compound with the active site histidine. These types of attachments are described below. However, as noted above, the interaction need not be perfect to allow inhibition, since it appears that increasing the local concentration of the cobalt compound near the active site is sufficient.

Thus, the present invention allows a known enzymatic substrate to be used as an inhibitor, as well as increasing the efficiency of known inhibitors, for example via decreasing the $K_i$. A wide variety of enzyme substrates and inhibitors for a variety of proteases containing either an active site histidine or an essential metal ion coordinated by a histidine are known in the art. In addition, the morphological properties of enzymes for which the crystal structures are known are used to design appropriate cobalt compounds. Alternative embodiments utilize known characteristics about surface charge and hydrophobicity, and substrate and inhibitor specificity.

In a preferred embodiment, the $K_1$ of the polypeptide inhibitor is decreased as a result of attachment to the cobalt compound. That is, the inhibitor becomes a better inhibitor as a result of the attachment of the cobalt compound. Thus, the cobalt compound is effective at lower concentrations since fewer molecules are wasted at other sites.

In a preferred embodiment, at least one of the R groups is a nucleic acid used to target the cobalt compound to a particular protein or enzyme. For example, the target protein can be a nucleic acid binding protein that has at least one histidine that is important in biological activity, such as a zinc finger protein (see Louie and Meade, (1998) *Proc. Natl. Acad. Sci. USA* 95:6663–6668, herein incorporated by reference in its entirety).

As with the polypeptides, the cobalt compound can be attached to the nucleic acid in a variety of ways in a variety of positions; the actual methods are described below. The attachment site is chosen to maximize the interaction of a cobalt-reactive amino acid such as histidine that is essential for metal ion binding (or an active site histidine) with the cobalt compound. In a preferred embodiment, the backbone of the nucleic acid is modified to contain a functional group that can be used for attachment to the cobalt compound. This functional group may be added to either the 5' or 3' end of the nucleic acid, or to an internal nucleotide. For example, the nucleic acid may be synthesized to contain amino-modified nucleotides using techniques well known in the art (see for example Imazawa et al., *J. Org. Chem.* 44:2039–2041 (1979); Miller et al., *Nucleosides, Nucleotides* 12:785–792 (1993); and WO95/15971, and references cited therein). In this embodiment, amine groups are added to the ribophosphate backbone at the 2' or 3' position, thus allowing the attachment of the nucleic acid to the cobalt at either the 5' or 3' end, or to an internal nucleotide. These amine groups are then used to couple the nucleic acid to the cobalt compound. Alternatively, nucleotide dimers, containing phosphoramide, phosphorothioate, phosphorodithioate, or O-methylphosphoroamidite linkages may be made, and added to the nucleic acid at any position during synthesis, and the nitrogen or sulfur atom used for attachment using well known techniques, as outlined below. Additionally, the phosphorus atom of the backbone may be used, or linkers, as is known in the art (see for example Thuong et al., Angew. Chem. Int. Ed. Intl. 32:666–690 (1993); and Mergny et al., Nucleic Acid Res. 22:920–928 (1994)).

Complexes stabilized by invention methods are soluble in aqueous solution. As used herein, the term "soluble in aqueous solution" means that the Co(III) compound has appreciable solubility in aqueous solution and other physiological buffers and solutions. Solubility may be measured in a variety of ways. Solubility is measured using the United States Pharmacopeia solubility classifications, with the Co(III) compound being either very soluble (requiring less than one part of solvent for 1 part of solute), freely soluble (requiring one to ten parts solvent per 1 part solute), soluble (requiring ten to thirty parts solvent per 1 part solute), sparingly soluble (requiring 30 to 100 parts solvent per 1 part solute), or slightly soluble (requiring 100–1000 parts solvent per 1 part solute). Alternatively, since cobalt containing compounds are generally colored, the appearance of a color upon addition to a colorless aqueous solution indicates an acceptable level of solubility. For example, certain Co(III) complexes appear purple or appear orange when in solution.

Testing whether a particular Co(III) compound is soluble in aqueous solution is routine, as will be appreciated by those in the art. For example, as noted above, the appearance of a Schiff base Co(III) complex color upon addition to a colorless aqueous solution indicates solubility. Alternatively, the parts of solvent required to solubilize a single part of Co(III) compound may be measured, or solubility in gm/ml may be determined.

In a preferred embodiment where targeting of the cobalt complexes depicted in Formula A is desired, the cobalt complexes have a regiospecific hydrophilicity. That is, $R_1$ to $R_4$, are either hydrogen, alkyl or aryl, and are therefore hydrophobic, and at least one of $R_5$, $R_6$, $R_7$ and $R_8$ is hydrophilic. However, other combinations resulting in amphiphathic characteristics are also possible, as will be appreciated by those in the art. This is particularly desirable since this regiospecific hydrophilicity allows better positioning of the cobalt compound in or near the active site or on the surface of a protein or enzyme.

Particularly preferred embodiments of the present invention include Structure A, wherein $R_1$ is n-propyl alcohol, $R_2$ is hydrogen, $R_3$ is methyl, $R_6$ is methyl, $R_7$ is hydrogen, $R_8$ is methyl, and $R_4$ and $R_5$ are hydrogen:

The addition of electron donating or electron withdrawing groups may affect the activity of the cobalt compound with respect to the ability to exchange an axial ligand. For example, the addition of trifluoromethyl R groups at the $R_1$ and $R_8$ positions basically eliminates the reactivity of the Co(III) compound towards new axial ligands. Electron withdrawing or donating groups are preferably added at the $R_1$ and/or $R_8$ positions, as this is easiest for synthesis, as well as the preferred position for electronic coupling. The $R_2$ and/or $R_7$ positions are also preferred. It is also possible to put electron donating groups at the $R_3$ and $R_6$ positions, but if $R_3$ and/or $R_6$ contain an electron withdrawing group then the compound may be difficult to synthesize using the schemes depicted herein. Suitable electron withdrawing groups include, but are not limited to, halides (F, Cl, Br, I, in decreasing order of electron withdrawing strength), phenyl and substituted phenyl groups such as nitro-phenyl, amines and quaternary amines, thiols, nitro groups, carboxy groups, nitrile, alkynes and alkanes, sulfonyls, and others known in the art. Suitable electron donating groups include, but are not limited to, —$OCH_3$, methyl, carboxylate, and ether.

Generally, the cobalt compounds of the invention are synthesized as generically disclosed below in Scheme 1, using the general methods of Costa et al., J. Organometal. Chem., 6:181 (1966), which describes the preparation of derivatives of the components used to make the ligands used in the invention, such as acetylacetone etlhylenediamine (acacen).

Scheme I

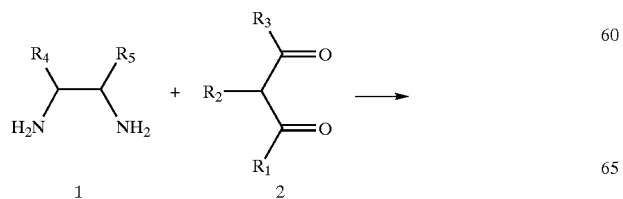

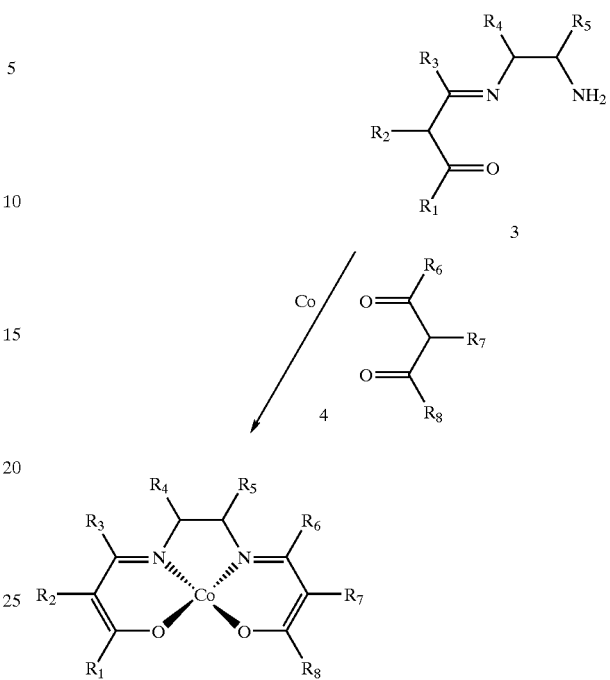

Compounds 1 (etlhylenediamine, "en"), 2 and 4 are generally made using techniques well known in the art. Compounds 2 and 4 are aliphatic beta-diketones, and compound 2 is an aliphatic amine. It will be understood by those skilled in the art that compounds 2, 3 and 4 are the resonance structures of compounds 6, 7, and 8 shown below in Scheme II. Compounds 6 and 8 are acetylacetone derivatives ("acac"), and compound 7 is the "monoacacen" product Scheme II

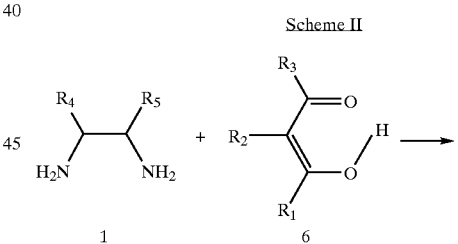

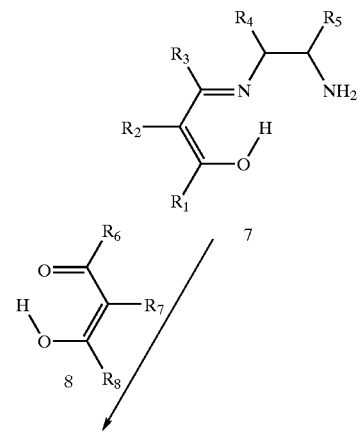

-continued

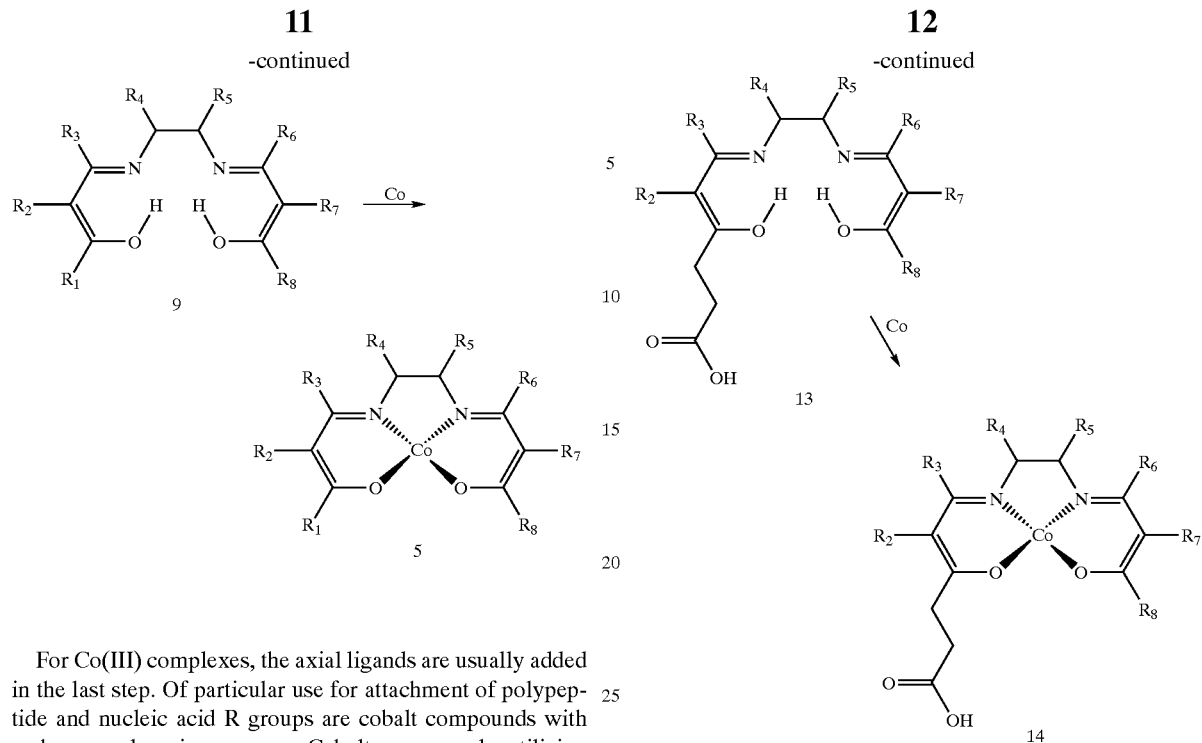

For Co(III) complexes, the axial ligands are usually added in the last step. Of particular use for attachment of polypeptide and nucleic acid R groups are cobalt compounds with carboxy and amino groups. Cobalt compounds utilizing carboxylic acids are synthesized as depicted below in Scheme III:

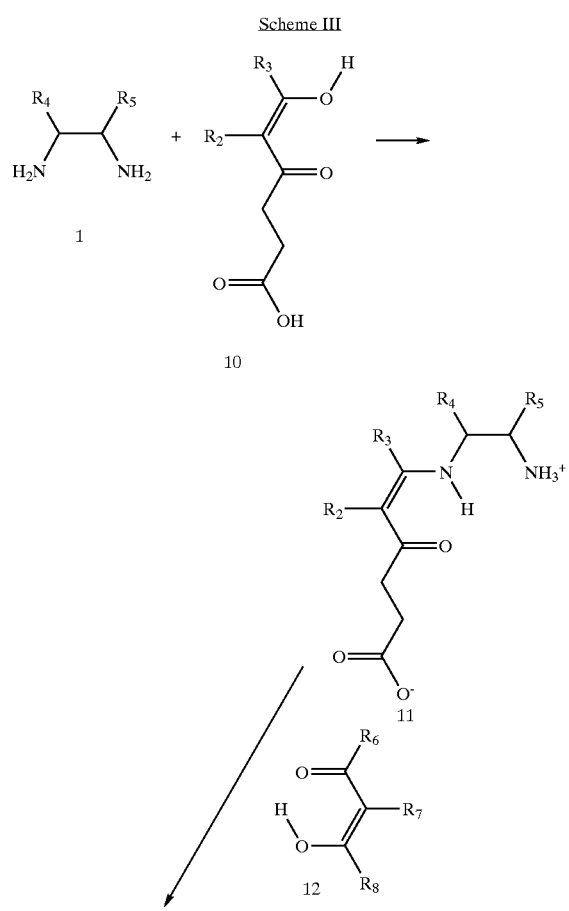

The amino-derivative of the core cobalt compound is synthesized as shown in Scheme IV at col. 14–15 from U.S. Pat No. 6,008,190, herein incorporated by reference in its entirety.

The NCS group may then be used for coupling, as is known in the art.

In the case where the R group is a polypeptide or nucleic acid, the cobalt compounds are generally constructed in three phases. First, the core cobalt compound is synthesized with a functional moiety that can be used to couple the polypeptide or nucleic acid. For example, the core cobalt compound is made with an amine, a carboxy or a sulfhydryl group. Next, the R group, comprising a polypeptide or nucleic acid, is made, which also contains a functional moiety that can be used for attachment. In some instances, other reactive groups of the polypeptide or nucleic acid are protected to prevent them from reacting with the functional group of the core cobalt compound. For example, amino acid side chains containing amino groups, such as arginine, may need to be protected to prevent the side chain from reacting, although in some embodiments the attachment is done via a functional moiety of an amino acid side chain. Protecting groups and techniques are well known in the art. Once the core cobalt compound and the R group are made, they can be attached by reacting the functional groups. In some instances, the linkage is direct; for example a cobalt compound containing a carboxy R group may be directly linked to an amino terminus of a polypeptide, as is depicted in the Examples. C-terminal attachment may be done using a cobalt compound with a amino functional moiety. As is known in the art, this direct linkage may be done in organic solvents or alternatively using coupling reagents such as 1-(3-dimethylaminopropyl )-3-ethylcarboiimide (EDC) (see generally, March, Advanced Organic Chemistry, 3rd Ed. Kiley & Sons. Inc. (1985); see also the 1994 Pierce Chemical Company catalog, technical section on cross-linkers, pages 155–200, incorporated herein by reference).

In a preferred embodiment, the linkage between the two functional moieties may utilize a linker, also well known in the art. For example, two amino groups may be linked via a stable bifunctional groups as are well known in the art, including homobifunctional and heterobifunctional linkers (see Pierce Catalog and Handbook, pages 155–200). In an additional embodiment, carboxy groups (either from the polymer or from the cell targeting moiety) may be derivatized using well known linkers (see the Pierce catalog). For example, carbodiimides activate carboxy groups for attack by good nucleophiles such as amines (see Torchilin et al. Critical Rev. Therapeutic Drug Carrier Systems, 7(4):275–308 (1991), expressly incorporated herein). Sulfhydryl groups may be added to amines or carboxy groups with heterobifunctional linkers (see the Pierce catalog).

It should be understood that the attachment can be done in a variety of ways, including those listed above. What is important is that manner of attachment does not significantly alter the functionality of the polypeptide or nucleic acid; that is, they are still able to bind to the target protein. As will be appreciated by those in the art, this is easily verified.

As will be appreciated in the art, a number of functional groups of the polypeptide and nucleic acid may be used for covalent coupling. Alternatively, the polypeptide may be derivatized to contain a functional moiety, such as through the addition of a linker containing a functional moiety. When a polypeptide is to be used as an R group, a preferred embodiment utilizes an amino group of the polypeptide. The N-terminal amino group may be used, or alternatively, an amino group of an amino acid side chain, such as the amine groups of arginine, asparagine, glutamine, lysine, histidine and tryptophan. Similarly, the linkage may be accomplished using the sulfur atoms of the side chains of methionine or cysteine. The carboxy groups of the side chains of glutamic acid and aspartic acid may also be used.

When the R group is a nucleic acid, a variety of positions may be used as the site of covalent attachment to the cobalt compound. In a preferred embodiment, the ribophosphate backbone of the nucleic acid is modified to contain a functional moiety (see for example Meade et al. *Angewandte Chemie*, English Edition, 34(3):352–354 (1995), and references cited therein; Imazawa et al. supra, Miller et al., supra.). For example, in a preferred embodiment, an amino group is added at the 2' or 3' position of the sugar using techniques well known in the art. In one embodiment, this is done by adding additional nucleotides that have an amino group to the nucleic acid; that is, as shown in the Examples, one or more "extra" nucleotides is added to the targeting nucleic acid. Alternatively, the phosphodiester linkage between two nucleotides may be altered to form phosphoramide, phosphorothioate, phosphorodithioate, or O-methylphosphoroamidite linkages, as is known in the art. The nitrogen or sulfur atoms are then used as functional moieties. The nucleotide dimer, containing the altered linkage, may be added to the nucleotide at any position. Functional groups on the nucleotide bases themselves may also be used, such as the amino groups on adenosine and cytosine, or modified bases such as is known for thymine (see for example Telser et al., *J. Amer. Chem. Soc.* 111:7221–7226 (1991); Unglisch et al., *Angew. Chem.* 103:629–646 (1991); *Angew. Chem. Int. Ed. Engl.* 30:613–629 (1991); Goodchild, *Bioconjugate Chem.* 1:165–187 (1990); and Brun et al., *J. Amer. Chem. Soc.* 113:8153–8159 (1991)). Then the nucleic acid containing the functional group may be added to the cobalt compound either directly or via a linker, as is outlined above for polypeptides.

The stabilized compounds can be assayed for antiviral, antimicrobial and antibacterial activity using techniques well known in the art; for example, bactericidal activity may be measured using the techniques outlined in example VI of U.S. Pat. No. 5,049,557. Both in vitro and in vivo antiviral activity may be measured using the techniques outlined in U.S. Pat. No. 5,210,096.

The compounds of the present invention may be formulated into pharmaceutical compositions, and administered in therapeutically effective dosages. As used herein, the term "therapeutically effective dose" refers to a dose that produces the effects for which it is administered. The exact dose will depend on the disorder to be treated and the protein to be inhibited, and will be ascertainable by one skilled in the art using known techniques. In a preferred embodiment, the pharmaceutical compositions of the invention are in a water soluble form, and contain a pharmaceutically acceptable carrier in addition to the cobalt compound. The pharmaceutical compositions may be administered in a variety of ways, including, but not limited to, orally, subcutaneously, intravenously, intraperitoneally, or topically.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes.

EXAMPLES

Example 1

Synthesis of Cobalt Compounds

Schiff base complexes were synthesized as described in Bottcher et al. (*Inorg. Chem.*, (1997) 36:2498–2504, herein incorporated by reference in its entirety).

Tris(hydroxymethyl)aminomethane (Tris, Trizma Base), polyethylene glycol (PEG 8000) and 1-(3-dimethylaminopropyl)-3-ethylcarboiimide (EDC) were obtained from Sigma (St. Louis, Mo.).

N-(2-hydroxyethyl)piperazine-N'-2-ethanesulfonic acid (HEPES) was from J. T. Baker Phillipsburg, N.J.). Cobaltous acetate tetrahydrate was obtained from FM Science (Gibbstown, N.J.). Human a-thrombin and the assay agent Spectrozyme (H-D-hexahydrotyrosyl-L-alanyl-L-arginine-p-nitroaniline diacetate) were purchased from American Diagnostica (Greenwich, Conn.). Antithrombotic peptides were manufactured as amides by the Beckman Institute Biopolymer Synthesis group at Caltech using solid phase methods. Weak cation exchange resin Sephadex G-25 was from Pharmacia (Uppsala, Sweden). Enzyme reactions were followed spectrophotometrically using a photodiode array spectrophotometer. Ultrafiltration materials were from Amicon (Beverly Mass.). HPLC used Vydac reverse phase columns. $^1$H NMR were obtained on a 300 MHz FT-NMR spectrometer. Solvents used include EM Omnisolve MeOH, Omnisolve $CH_2 Cl_3$ passed over basic alumina to remove residual acid, Fluka (Bubcs. Switzerland) puriss. MeOH and dioxane, and Quantum Chemical (Tuscola, Ill.) absolute EtOH. Distilled water was prepared by a Barmistead Nanopure system. All other solvents were reagent trade.

Synthesis of hydroxypropyl acacen

To 200 mL of deoxygenated $CH_2, Cl_2$ was added 10 mL of acetyl acetone (0.0974 mol) and cannulated into a 250 ml. addition funnel, which was attached to a 500 mL 3-neck roundbottom flask containing 100 ml. of deoxygenated $CH_2, Cl_2$ and 32.6 mL etlhylenediamine (en, 0.488 mol). The solution containing the acetyl acetone was added dropwise to the en solution. The reaction mixture was extracted with two 50 ml. portions of 0.2 NaPi, pH 5.5. The organic layer was separated and placed in a −20° C. freezer overnight. The resulting solution was filtered through fluted filter paper and the solvent was removed in vacuo. The compound was further purified using flash silica gel chromatography using 95:5:0.5 (v:v:v) $CH_2Cl_2$:MeOH:$Et_3$N as the eluant. The resulting monoacacen was characterized by NMR.

Monoacacen (0.5 g, 3.5. times.$10^{-3}$ mol) was dissolved in 5 mL of ethanol and 7-hydroxy-2,4-heptanedione (0.51 g. 3.5. times.$10^{-3}$ mol) was added. The dione was synthesized as described previously (Detty, M. R. J. Org. Chem., 44:2073–2077 (1979)). The reaction was allowed to proceed for 4 hours and the solvent was removed in vacuo. The sample was purified using flash silica gel chromatography using 93:7 (v:v) $Cl_2Cl_2$,:MeOH as the eluant. The resulting hydroxypropyl acacen was characterized by NMR.

Synthesis of Co(II)hydroxypropyl acacen

Hydroxypropyl acacen (0.25 g, 9.4. times.$10^{-4}$ mol) was dissolved in 2 mil of deoxygenated methanol in an inert atmosphere glove box. To this solution was added CO(II) ($CH_3COO$—)$_2$ ($H_2O$)$_4$ (0.2338 g, 9.4. times.$10^{-4}$ mol). The mixture was allowed to stir for an additional thirty minutes. The reaction vessel was sealed and the solvent was removed in in vacuo. The compound was used without further purification.

Synthesis of [Co(III)hydroxypropylacacen($NH_3$)$_2$]$CH_3COO$

Hydroxypropyl acacen was reacted with Co(acetate) as described earlier. However after the reaction vessel was sealed, anhydrous ammonia gas was bubbled through the reaction mixture and subsequently exposed to air. The solvent was removed in vacuo, and the product was purified using an alumina column with neat methanol as the eluant. The sample was characterized by NMR.

Synthesis of Acacen

To 20 mL of ethanol was added 20 mL of acetyl acetone (0.0973 mol). To this solution was added 6.5 mL of ethylenediamine (0.0973 mol) using an addition funnel. The solution was placed in a refrigerator at 4° C. overnight, and the crystals were triturated three times with anhydrous diethylether (MP=110.1–111.1).

Synthesis of [Co(III)Acacen($NH_3$)$_2$]Cl 249.08 g of cobalt acetate, 6 $H_2$O, (1 mol) was dissolved in 1.750 L methanol and the solution was filtered through Whatman paper No. 1. Acacen (1 mol) was suspended in 150 mL methanol. Nitrogen dried by passage through a silica gel dessicant column was bubbled over the reagents for 15 minutes. The cobalt acetate solution was added dropwise (½ hour) and the orange-brown solution was left to react at room temperature under nitrogen for 2 hours. The flask was opened to air and $NH_3$ gas was bubbled into the solution; the mixture was concentrated on a rotary evaporator. An equivalent of sodium chloride dissolved in a minimum amount of water was added, poured into a wide vessel, and left to crystallize slowly. The brown crystalline powder was filtered, washed with methanol and dried.

Further synthesis of assymetrical or "mixed" ligands "Acacen" (compound 9 in Scheme II): 1 equivalent ethylenediamine in anhydrous EtOH was added to 2 equivalents acetylacetone in EtOH with stirring. After 30 minutes, the mixture was put in the freezer to precipitate a white crystalline solid. The product was collected by vacuum filtration over a coarse glass frit and rinsed with diethyl ether. It can be recrystallized from benzene to desired purity. Purified crystals melted at 111° C.

"Monoacacen" (compound 7 in Scheme II): The 1:1 condensation product of acetyl acetone and en was prepared according to literature procedures (Cros et al., C. R. Acad. Sc., Ser. II 294:173 (1982)) substituting $CH_2Cl_2$, for chloroform. The resulting yellow oil often contained some acacen (about 10%), which could be removed by flash chromatography on silica using 97 $CH_2Cl_2$/3 MeOH/0.5 TEA either now or after the addition of another diketone.

"Bzacacacen" (the Formula 1 compound with R1, R3 and R6 as methyl, R2 and R7 as hydrogen, and $R_8$ as phenyl): 1 equiv. benzoylacetone in $CH_2Cl_2$ was added to a solution of monoacacen in $CH_2Cl_2$. Removal of solvent gave a white powder containing some acacen impurity. Purification was accomplished by flash chromatography on silica using 97 $CH_2Cl_2$/3 MeOH/ 0.5 TEA.

"Aciden" (compound 11 in Scheme III): A solution of 1 equiv. 4.6-dioxoheptanoic acid in $CH_2Cl_2$ was added to 1 equiv. ethylenediamine in $CH_2Cl_2$ and the insoluble 1:1 condensation product immediately precipitated. The product was collected over a frit and dried in vacuo. The melting point was 140° C., with decomposition. A direct reaction of 4,6-dioxoheptanoic acid with monoacacen did not work, despite repeated attempts. Evidently, the acid group was effecting decomposition, even under anhydrous conditions. Nor did using excess triethylamine to neutralize the diketoacid give satisfactory results. "Acacaciden" (compound 13 in Scheme III): 1 equiv. aciden was powdered and Slurried in Fluka puriss. MeOH. 1 equiv. triethylamine and 2–2.5 equivalents acetyl acetonewere added and the mixture was allowed to stir overnight to give a yellow solution. It was evaporated to dryness to obtain the crude product as an orange oil. Further purification by flash chromatography over silica using a 5% to 25% gradient of MeOH in $Cl_2Cl_2$ with 0.5% TEA to guard against hydrolysis of imine bonds. Evaporation of solvent followed by recrystallization from EtOH gave a beige solid. M' was 282, as expected.

[Co(III)(acacen)($NH_3$)$_2$]Cl: Procedure obtained from Zvi Dori (The Technion, Haifa, Israel. 1 equiv. of acacen was degassed in vacuo and placed under argon. Dry, degassed methanol was transferred into the flask via cannula. 1 equiv. cobaltous acetate was treated in same manner and the resulting purple solution added via cannula to the clear solution of the ligand. An immediate color change from purple to orange was observed as the reaction was stirred under argon for two hours. Ammonia gas was bubbled into the solution and the flask opened to air. Reaction was stirred with ammonia for 4 hours, evaporating solvent replenished as necessary. The reddish solution was filtered over a frit and concentrated on a hot plate. Addition of saturated aqueous NaCl precipitates the brown product. It can be recrystallized from ethanol to give a tan powder.

[Co(III)(acacaciden)($NH_3$)$_2$]: The above metallation conditions were used, but with the acacaciden ligand. Crude reaction mixture did not afford precipitate, but purification over cation exchange resin using aqueous ammonium acetate followed by removal of the volatile buffer gave a light brown powder. M' was 373, as expected.

Example 2

Synthesis of $N^1,N^2$-Bis(BOC)-$N^6$-Trityl-1,2,6-triaminohexane and $N^1,N^2$-Bis(BOC)-$N^6$-Trityl-1,2,6-triaminohexane $N^6$-Trityl-Lysine (2): Lysine 2HCL (1.012 g, 4.34 mmol) was suspended in 300 ml dichloromethane, and sonicated until suspension was homogeneous. Triethylamine (7.5 ml, 54.1 mmol, 2.5 eq.) was added and the mixture was left to stir for 20 minutes in Brine/Ice bath (−15° C). Triphenylmethylchloride (Trityl chloride) (6.00 g, 21.5 mmol, 1 eq.) was dissolved in 200 ml dichloromethane and then slowly added over a period of 1 hour via a dropping funnel to the reaction flask. The reaction was followed by TLC (Silica, 5% methanol/95% $CH_2Cl_2$) and was stopped 1 hour after disappearance of Trityl chloride. Volume was reduced by reduced pressure distillation. The reaction product was washed first with 5% sodium bicarbonate (2×, 20 ml each), brine (1×, 20 ml), dried over sodium sulfate, filtered, and the solvent removed at reduced pressure distillation. The product was purified by flash column chromatography (Silica Gel, 3% methanol/97% CH2Cl2) and isolated as a clear golden oil (0.753 g. Yield: 43%). 1H NMR (CDCl3, 300 MHz δ1.40 (m, 2H), 1.52 (m, 2H), 1.67 (m, 2H), 2.11 (t,2H), 3.41 (t, 1H), 3.69 (s,3H), 7.14–7.51 (m, 15H); $^{13}$C NMR (CDCl$_3$, 75 MHz) δ23.6, 30.7, 35.0, 43.5, 51.9, 54.5, 71.0, 126.2, 127.8, 128.7, 146.4, 176.6; ESI-MS calculated for $C_{27}H_{30}N_2O_2$ 402.53; found 403.6 [M$^+$+1].

N$^6$-Trityl-Lysinamide (3): A solution of compound 2 (1.49 g, 3.71 mmol) in 10 ml DMF was cooled to –78° C. in a pressure tube. Ammonia gas was bubbled though the solution until approximately 1 ml has added. Ammonium hydroxide solution (12 ml, 185.6 mmol, 50+ equivalents) was then added, and the tube allowed to warm to room temperature. The mixture was then sonicated for 20 minutes and heated to 55° C. while stirring. After 24 hours, the solution was golden in color, after which it was removed from the oil bath and cooled to –78° C. for 5 minutes before removing pressure cap. The solution was then allowed to warm to room temperature, and the solvent removed by reduced pressure distillation. The product was purified by flash column chromatography (Silica Gel, 8% methanol/92% CH$_2$Cl$_2$). and isolated as a clear golden oil (0.987 g. Yield: 68%). 1H NMR (CDCl3, 300 MHz) δ1.3–1.6 (m, 4H), 1.76 (m, 2H), 2.13 (t,2H), 3.33 (t, 1H) 7.14–7.52 (m, 15H) $^{13}$C NMR (CDCl$_3$) 75 MHz) δ23.8, 30.9, 35.2, 43.6, 55.3, 71.0, 126.3, 127.9, 128.8, 146.4, 178.3; ESI-MS calculated for $C_{25}H_{29}N_3O$ 387.52; found 388.4 [M$^+$+1].

N$^6$-Trityl-1,2,6-triaminohexane (4): To an oven dried pressure tube (sealed and under argon) with stirrer, was added a 1M solution of Borane:THF (26 ml, 26 mmol and cooled to –15° C. A solution of Compound 3 (2.56 g, 6.54 mmol) in 5 ml dry tetrahydrofuran was slowly added. After addition was complete, the solution was allowed to stir for 10 minutes, and then heated to 65° C. After 6 hours, the solution (colorless) was and cooled to –15° C. before opening, and then allowed to warm to room temperature. The excess borane was quenched with water (25 ml), and the solvent reduced by reduced pressure distillation. The solution was then brought to pH 13 by the addition of sodium hydroxide pellets, and extracted dichloromethane. The solution was dried over sodium sulfate, filtered, and the solvent removed by reduced pressure distillation. The product was purified by flash column chromatography (Aluminum Oxide, 8% methanol/92% CH$_2$Cl$_2$) and isolated as a white powder. (1.89 g. Yield: 78%). 1H NMR (CDCl$_3$, 300 MHz) δ 1.0–1.7 (m, 6H) 2.04 (br, 2H), 2.30 (m 1H), 2.51 (m, 2H), 7.00–7.60 (m, 15H) $^{13}$C NMR (CDCl$_3$, 75 MHz) δ 24.1, 31.1, 35.8, 43.6, 48.8, 53.7, 71.0, 126.7, 127.4, 128.4, 146.4; ESI-MS calculated for $C_{25}H_{31}N_3$ 373.54; found, 374.4 [M$^+$+1].

N1, N2-Bis(BOC)-N6-Trityl-1,2,6-triaminohexane (5): Compound 4 (0.920 g, 2.259 mmol) was added to 3.38 ml of a 10% solution of triethylamine in methanol, and the mixture was stirred until fully dissolved. Di-t-butyl dicarbonate (0.91 g, 4.5 mmol, 4 eq.) was added while stirring and then heated to reflux for 30 minutes, after which the solvent was removed by reduced pressure distillation. The resulting oil was dissolved in dichloromethane and washed with brine (3×125 ml), dried over sodium sulfate, filtered, and the solvent removed by reduced pressure distillation. The product was purified by flash column chromatography (Silica Gel, 2% methanol/98% CH$_2$Cl$_2$) and isolated as a white powder (0.454 g. Yield: 35%). $^1$H NMR (CDCl$_3$, 300 MHz) δ 1.0–1.5 (m, 4H), 1.43 (s, 18H), 1.60 (s, 2H) 2.10 (tr, 2H), 3.13 (br, 2H), 357 (br,1H), 7.00–7.60 (m,15H); $^{13}$C NMR (CDCl$_3$, 75 MHz) δ No Data ESI-MS calculated for $C_{35}H_{47}N_3O_4$ 573.77; found 574.6 [M$^+$+1].

N$^1$,N$^2$-Bis(CBZ)-N$^6$-Trityl-1,2,6-triaminohexane (6): Compound 4 (300 mg, 0.81 mmol), dimethylaminopyridine (20 mg, 0.16 mmol, 0.2 eq), and triethylamine (0.5 ml, 3.5 mmol, 4.3equivalents) were dissolved in dry DMSO (3 ml). Cooled to 0° C. While stirring, benzylchloroformate (0.51 ml, 3.6 mmol, 4.4equivalents) was added dropwise. Stirred for 2.5 hours at 40° C. and followed by TLC (Silica, 10% methanol:methylene chloride). Diluted with 10 ml methylene chloride and extracted twice with 5% sodium bicarbonate (20 ml each) and once with brine solution (10 ml). Purified by flash column chromatography (Silica gel, 3% methanol:methylene chloride).

What is claimed is:

1. A compound having the structure:

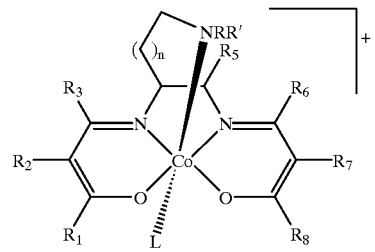

wherein:

L is NHRR'; and each R and R' are independently selected from hydrogen and substituted or unsubstituted alkyl, substituted or unsubstituted alkenyl, substituted or unsubstituted alkynyl, substituted or unsubstituted cycloalkyl, ester, alkoxy, ether; or R and R' can cooperate to form a substituted or unsubstituted heterocycle optionally having one or more double bonds; and $R_1$, $R_2$, $R_3$, $R_5$, $R_6$, $R_7$ and $R_8$ are independently selected from hydrogen, substituted or unsubstituted alkyl, substituted or unsubstituted alkenyl, substituted or unsubstituted alkynyl, substituted or unsubstituted cycloalkyl, ester, alkoxy, ether, hydrophilic organic acid, amine, alkyl amine, alcohol, and aryl;

n is 1, 2, 3, 4, 5, 6, 7, or 8.

2. The compound of claim 1, wherein each R and R' are both hydrogen.

3. The compound of claim 1, wherein R is hydrogen and R' is $(C_6H_5)_3C$—.

4. The compound of claim 1, wherein each R and R' cooperate to form imidazole and n is 1.

5. The compound of claim 1, wherein L is NH$_3$ and R and R' cooperate to form imidazole.

6. The compound of claim 1, wherein L is 2-methyl imidazole.

7. A method of increasing the stability in aqueous media of a cobalt(III) Schiff base complex comprising:

(a) obtaining a compound having the structure:

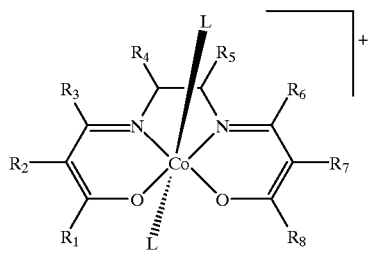

wherein one axial ligand position (L) is NHRR' or 2-methylimidazole,
  wherein R and R' are independently selected from hydrogen and substituted or unsubstituted alkyl, substituted or unsubstituted alkenyl, substituted or unsubstituted alkynyl, substituted or unsubstituted cycloalkyl, ester, alkoxy, ether; and
  $R_1$, $R_2$, $R_3$, $R_4$, $R_5$, $R_6$, $R_7$ and $R_8$ are independently selected from hydrogen, substituted or unsubstituted alkyl, substituted or unsubstituted alkenyl, substituted or unsubstituted alkynyl, substituted or unsubstituted cycloalkyl, ester, alkoxy, ether, hydrophilic organic acid, amine, alkyl amine, alcohol, and aryl; and (b) adding a linker that connects $R_1$ with the remaining axial ligand position (L) wherein,
  the linker has the formula —$(CH_2)_n$—NR"R'"
  wherein n is 1, 2, 3, 4, 5, 6, 7 or 8 and
  R" and R'" are independently selected from hydrogen and substituted or unsubstituted alkyl, substituted or unsubstituted alkenyl, substituted or unsubstituted alkynyl, substituted or unsubstituted cycloalkyl; or R" and R'" can cooperate to form a substituted or unsubstituted heterocycle optionally having one or more double bonds.

8. The method of claim 7, wherein n is 3, 4 or 5, and R, R', R" and R'" are hydrogen.

9. The method of claim 7, wherein n is 2, 3 or 4, R and R' cooperate to form 2-methylimidazole, and R" and R'" cooperate to form imidazole.

10. The method of claim 7, wherein n is 3, 4, or 5, and R, and R' are hydrogen, and R" and R'" cooperate to form imidazole.

11. A method of increasing the stability in an aqueous medium of a cobalt(III) Schiff base complex comprising:
  (a) obtaining a cobalt(III) Schiff base complex having the structure:

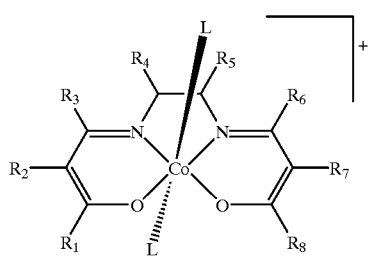

wherein a first axial position (L) and a second axial position (L) are independently selected from NHRR', wherein each R and R' are independently selected from hydrogen and substituted or unsubstituted alkyl, substituted or unsubstituted alkenyl, substituted or unsubstituted alkynyl, substituted or unsubstituted cycloalkyl, ester, alkoxy, ether; or R and R' can cooperate to form a substituted or unsubstituted heterocycle optionally having one or more double bonds; and $R_1$, $R_2$, $R_3$, $R_4$, $R_5$, $R_6$, $R_7$ and $R_8$ are independently selected from hydrogen, substituted or unsubstituted alkyl, substituted or unsubstituted alkenyl, substituted or unsubstituted alkynyl, substituted or unsubstituted cycloalkyl, ester, alkoxy, ether, hydrophilic organic acid, amine, alkyl amine, alcohol, and aryl; and (b) contacting the cobalt(III) Schiff base complex with a linker that connects the first and second axial positions, wherein the chelator has the structure:

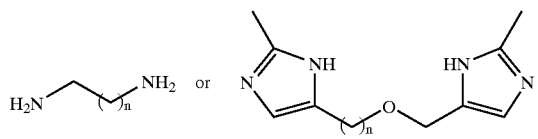

wherein n is 2, 3, 4, 5, 6, 7, or 8.

12. The method of claim 11, wherein at least one L is $NH_3$ or a substituted or unsubstituted imidazole.

13. The method of claim 11, wherein the first axial positions and the second axial position are contained in the same Schiff base complex molecule.

14. The method of claim 11, wherein the first axial position is in a first Schiff base complex molecule and the second axial position is in a second Schiff base complex molecule.

15. A method of increasing the stability in an aqueous medium of complexes of Cobalt (III) Schiff-bases complexes comprising contacting the Schiff base complex with a bidentate having from about three to eight $CH_2$ units that can bind to a first axial ligand position and a second ligand position.

16. The method of claim 15, wherein the linker is

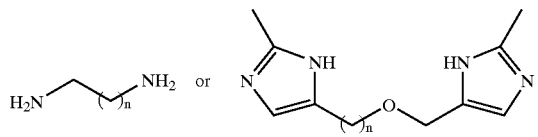

wherein n is 2, 3, 4, 5, 6, 7 or 8.

* * * * *